United States Patent [19]

Scharf

[11] Patent Number: 5,425,640
[45] Date of Patent: Jun. 20, 1995

[54] METHOD AND PRODUCT FOR IMPROVED CERAMIC FIBER REINFORCED AND FILLED THERMOPLASTIC AND THERMOSETTING RESIN SYSTEMS

[76] Inventor: Jonathan Scharf, 364-A7 St. Andrews Rd., Glenmoore, Pa. 19343

[21] Appl. No.: 965,686

[22] Filed: Oct. 22, 1992

[51] Int. Cl.$^6$ ............................................. A61C 5/00
[52] U.S. Cl. ................................ 433/215; 427/299; 427/309; 428/367; 433/9; 433/226
[58] Field of Search .................... 427/297, 389.8; 428/367; 433/180, 215, 9, 226; 422/309

[56] References Cited

U.S. PATENT DOCUMENTS

| | | | |
|---|---|---|---|
| 2,700,010 | 1/1955 | Balz | 154/128 |
| 3,637,550 | 1/1972 | Sprauer | 156/332 X |
| 4,274,907 | 6/1981 | Vig et al. | 156/645 X |
| 4,292,236 | 9/1981 | Ibsen et al. | 264/36 X |
| 4,364,231 | 12/1982 | Norling et al. | 433/218 |
| 4,415,404 | 11/1983 | Riegl | 156/635 |
| 4,473,353 | 9/1984 | Greggs | 433/215 |
| 4,632,660 | 12/1986 | Jurim | 433/215 |
| 4,654,007 | 3/1987 | Sigler et al. | 433/236 |
| 4,710,217 | 12/1987 | Bailey et al. | 65/31 |
| 4,728,291 | 3/1988 | Golub | 433/215 |
| 4,793,809 | 12/1988 | Sigler et al. | 433/202.1 X |
| 4,799,888 | 1/1989 | Golub | 433/215 |
| 5,098,304 | 3/1992 | Scharf | 433/215 |
| 5,139,188 | 8/1992 | Scharf | 224/217 |

OTHER PUBLICATIONS

"Nextel ™ Ceramic Fiber Products"—3M Corporation, no date.
"JPS Astroquartz ® III" Product Information—JPS Glass Fabrics, Mar. 6, 1991.
"Astroquartz ® Composite and Conform ™ Industrial Fabrics"—JPS Glass Fabrics, no date.
"Dictionary of Fiber & Textile Technology"—Hoechst Celanese Corporation, 1990, pp. 22–25, 72–73 and 124–125.
"Polycrystalline Alumina and Zirconia Fibers for High--Temperature Applications" M. J. Morton and S. P. Hepburn, 1974.
"Textile Fibers for Industry"—Owens-Corning Fiberglas Corporation, 1983.
"Effect of porcelain surface treatment on the bond to composite," *The Journal of Prosthetic Dentistry*, vol. 60, No. 3, Sep. 1988-Alton M. Lacy, M.S., Ph.D., D.D.S.; Jose LaLuz; Larry G. Watanabe, B.S.; and Mark Dellingers, D.D.S.
"In vitro effect of topical fluoride on dental porcelain," *The Journal of Prosthetic Dentistry*, vol. 55, No. 3, Mar. 1986—Richard C. Wunderlich, D.D.S., M.S. and Peter Yaman, D.D.S., M.S.
"DICOR ® Surface Treatments for Enhanced Bonding," *J Dent Res*, vol. 67, No. 6 Jun. 1988—L. F. Bailey and R. J. Bennett.
"Decrease in reflectance of porcelains treated with APF gels," *Dental Materials*, vol. 4, pp. 289–295, 1988—Gonzalez, E., Naleway, C A, Fan P L, Jaselskis T.
"Etching effect of topical fluorides on dental porcelains: A preliminary study," *J. Canada Dent Assn*, No. 6, 1973-D. J. Gau, D.D.S., E. A. Krause.
"Effect of air–powder abrasive instrument on porcelain," *Journal of Prosthetic Dentistry*, vol. 60, No. 4, Oct. 1988-Robert L. Cooley, D.M.D., M.S.; Richard M.

(List continued on next page.)

*Primary Examiner*—Michael Lusignan
*Attorney, Agent, or Firm*—Michael F. Petock

[57] ABSTRACT

A method and product for improved ceramic fiber reinforced and/or filled thermoplastic and/or thermosetting resin systems utilizes ceramic fiber material which is first etched and then silanated using an organo-functional silane. The etching of the ceramic fiber may be performed utilizing hydrofluoric acid, acidulated phosphate fluoride or the equivalent thereof. The term ceramic fibers is used broadly to include all types of fibers which are made from substantially pure or pure silica, various silicates, metal oxides and other fibers, such as carbon, which are coated or provided with a silica treatment on their surface.

26 Claims, No Drawings

OTHER PUBLICATIONS

Lubow, D.M.D., M.S.; Frederic H. Brown, D.M.D., M.S.

Abstracts from *Craniofacial Biology/Dental Materials*, p. 245, Nos. 1105–1112.

Abstracts from *IADR AADR Abstracts 1985*, p. 296, Nos. 1089–1097.

"Effects of topical fluorides on five low-fusing dental porcelains," *The Journal of Prosthetic Dentistry*, vol. 52, No. 3, Sep. 1984—Daniel P. Copps, D.D.S.; Alton M. Lacy, Ph.D., D.D.S.; Thomas Curtis, D.D.S.; and John E. Carman, D.D.S.

"The Silk Wrap Technique for Composite Bonding," *The New York State Dental Journal*, vol. 53, No. 5, May 1987—Jeff Evans Golub, D.D.S.

"The Manhattan bridge: a new silk-wrap technique," *Dental Abstracts*, vol.32, No. 2, Feb. 1987—J. E. Golub.

"Smile Makeovers," *McCall's* magazine, Feb. 1987—Golub.

Single page entitled "SILKWRAP The Silk-Bonded Restorative" by Dentique, Inc. no date.

"Porcelain-to-composite bond strengths using four organosilane materials," *Journal of Prosthetic Dentistry*, vol. 61, No. 2, Feb. 1989—J. H. Bailey, D.D.S.

"Composite Resin Repair of Porcelain Using Different Bonding Materials," *Operative Dentistry*, vol.13, pp. 114–118—Gregory et al, no date.

"Tensile Bond Strengths of Five Porcelain Repair Systems," *Operative Dentistry*, vol. 13, pp. 162–167, 1988—Cochran et al.

"Bond Strengths of intraoral porcelain repair materials," *The Journal of Prosthetic Dentistry*, vol. 61, No. 3, Mar. 1989—Diaz-Arnold et al.

"Repairing Porcelain" under heading *The Reviews* of a monthly update to *Reality Now/The information source for esthetic dentistry*, No. 3, Mar. 1989, by Diaz-Arnold, A. M. et al. (subtitle: Are Silanes Really Different?).

"Luting interfaces and materials for etched porcelain restorations. A status report for the American Journal of Dentistry," *American Journal of Dentistry*, vol. 1, No. 5, Oct. 1988—Sheth and Jensen.

*Theory of Mechanisms of Silane Coupling Agents in Glass Reinforced and Filled Thermoplastic and Thermosetting Resin Systems*, Sterman and Marsden, Union Carbide Corporation/Adhesion Promoters, no date.

Organofunctional Silanes—A Profile, Union Carbide Corporation/Silicones and Urethane Intermediates, no date.

"Functions, applications and advantages of silane coupling agents," reprinted from *Plastics Compounding* for Resin Producers, Formulators and Compounders, Jul.-/Aug. 1978 by James Marsden for Union Carbide Corporation.

Brochure entitled *Union Carbide Silicones Organofunctional Silanes Product Information*, "Union Carbide Organofunctional Silane A-1130," Form F-47770, Dec. 1980, 4M.

Book entitled *REALITY/The information source for esthetic dentistry*, vol. 4, No. 1, 1989, edited by Esthetic Dentistry Research Group, pp. 80–81, 145–146, and 205–206.

METHOD AND PRODUCT FOR IMPROVED CERAMIC FIBER REINFORCED AND FILLED THERMOPLASTIC AND THERMOSETTING RESIN SYSTEMS

BACKGROUND OF THE INVENTION

The present invention relates to an improved method and product for creating fiber reinforced and/or filled thermoplastic and/or thermosetting resin systems. More particularly, the present invention is directed to such resin systems which are usable in higher temperature applications.

Glass fiber reinforced resin systems are widely used today for everything from boat hulls, automobile bodies, toys, sliding boards and the like.

SUMMARY OF THE INVENTION

The present invention provides an improved product and method of manufacturing a resin system which may be utilized in high temperature applications in everything from porcelain veneers and replacement teeth in dentistry to components used in connection with combustion engines. The present invention provides improved temperature characteristics for all types of industrial uses of reinforced resin systems.

Briefly, in accordance with the present invention, a method and product are disclosed for providing improved ceramic fiber reinforced and filled thermoplastic and thermosetting resin systems, wherein the ceramic fiber material is first etched with hydrofluoric acid, acidulated phosphate fluoride or other suitable etchant to produce a roughened surface on the ceramic fiber material which promotes adhesion. Such roughened surface of the ceramic fiber provides improved bonding for additional strength. The etched ceramic fiber material, which may take various forms, is then silanated with a silane coupling agent and utilized in the production of a reinforced resin system which may be utilized in high temperature applications.

The term ceramic fiber is defined and used herein broadly to include various high temperature glassy type fibers which may be made from pure or substantially pure silica, various silicates, metal oxides and various other fibers provided with a coating or treatment of silica on their surface.

DETAILED DESCRIPTION OF THE PREFERRED EMBODIMENTS

The present invention relates to a method and product for improved ceramic fiber reinforced and filled thermoplastic and thermosetting resin systems, wherein the ceramic fiber material is first etched to produce a roughened surface on the ceramic fiber material. In other words, the etching produces microporosities in the surface of the ceramic material. In the presently preferred embodiments of the invention, the ceramic fiber material is etched with either hydrofluoric acid or 1.23% acidulated phosphate fluoride (or other suitable percentage). However, it is understood that other etchants, such as hot phosphoric acid, may be utilized which function in the same way to produce the same result.

The ceramic fiber material may be woven, braided or knitted cloth, uniform or random mesh, rope, thread or any other material made of ceramic fibers. The resins may be any of the various thermoplastic or thermosetting resins. However, in view of the particular application, wherein the ceramic reinforced resin system may be utilized in higher temperature settings, the resin should be selected to have suitable temperature characteristics.

The etched ceramic fiber material is then silanated with an organo-functional silane. Some examples of organo-functional silanes are vinyltrichlorosilane, vinyltriethoxy-silane, vinyl-tris(beta-methoxyethoxy)silane, gamma-MethacryloxyPropyltrimethyoxysilane, beta-(3,4-Epoxycyclohexyl)-ethyltrimethoxysilane, gamma-Glycidoxypropyltrimethoxysilane, gamma-Aminopropyltriethoxysilane, and N-beta-(aminoethyl)-gamma-aminopropyltrimethoxysilane. However, it is understood that other silane coupling agents may be used in practicing the present invention.

The organo-functional silanes act as coupling agents between the ceramic fiber material and the composite resin. A chemical bridge between the coupling agents and the ceramic substrates requires both a reactive silane and a reactive site on the ceramic surface. The number and arrangement of the reactive sites on the ceramic surface is increased by the etching process described herein.

Any suitable ceramic fiber material may be utilized in practicing the invention. The term "ceramic fibers" is used herein throughout broadly to cover all fibers which are referred to as ceramic fibers. These include, but are not limited to, fibers made from substantially pure or pure silica, various silicates, metal oxides and other fibers, such as carbon, which are coated or provided with a silica treatment on their surface. Some examples of ceramic fibers which may be utilized in the practicing of the present invention include aluminosilicate fibers and zirconia fibers. Such fibers are commercially available from Imperial Chemical Industries, Ltd. ("ICI") of Wilmington, Del. Other ceramic fibers which are currently available include high grade ceramic fibers sold under the trademark Nextel TM by 3M Corporation. One example of the composition of Nextel TM fibers is, by weight, 62% aluminum oxide ($Al_2O_3$), 14% boron oxide ($B_2O_3$) and 24% silicon dioxide ($SiO_2$). Another example of ceramic fibers usable in practicing the present invention are those sold by JPS Glass Fabrics, a division of JPS Converter and Industrial Corporation of Slater, South Carolina, under the trademark Astroquartz TM. The Astroquartz TM ceramic fibers are comprised of substantially pure silica (99.5% $SiO_2$). These are sometimes referred to as quartz fibers. An example of a fiber treated with silica on its surface is a carbon fiber treated with silica on its surface and sold under the trademark Nicalon TM commercially available from Nippon Carbon Co. of Japan, that is, it has a surface of ceramic material and a core of a different material.

In accordance with the present invention, a product and the method of providing improved ceramic fiber reinforced and filled resin systems are disclosed. The etched and silanated ceramic fiber may utilized in thermoplastic or thermosetting resins. The ceramic fiber material, whether it is in the form of a cloth, mesh, rope, thread or the like, is first etched to roughen its surface, which roughening may be observed under a microscope and may be described as microporosities. The etching may be performed using either hydrofluoric acid, 1.23% acidulated phosphate fluoride or any other suitable etchant. Any suitable silane coupling agent and particularly the organo-functional silanes may be utilized, and these include vinyltrichlorosilane, vinyltriethoxysilane, vinyl-tris(beta-methoxyethoxy)silane, gamma-methacryloxypropyltrimethoxysilane, beta-(3,4-Epoxycyclohexyl)-ethyltrimethoxysilane, gamma-Glycidoxypropyltrimethoxysilane, gamma-Aminopropyltriethoxysilane, and N-beta-(aminoethyl)-gamma-aminopropyltrimethoxysilane.

In a preferred embodiment, it is contemplated that the product of the ceramic fiber material may be provided in pre-etched form. That is, ceramic fiber woven material, mesh, rope or thread may be first treated with hydrofluoric acid and sold in that form for use in the production of an etched silanated ceramic fiber reinforced product. The ceramic fiber may be pre-etched and pre-silanated as sold.

The product and/or method of the present invention have wide application in various areas of industry, medicine and dentistry. The present invention may be used in any application of a fiber reinforced resin system, and is particularly useful where the reinforced resin system may be subjected to temperatures in excess of those appropriate for a fiberglass reinforced resin system. These include various components and parts in manufacturing processes, combustion engines, aerospace and various other applications.

In addition, the product and/or method of the present invention have specific application in the field of prosthetic dentistry, and more particularly, in the field of restorative and splinting operations in the field of dentistry using various reinforced resin systems. Attention is directed to my previously issued patent, U.S. Pat. No. 5,098,304, regarding the use in dentistry of composite resin reinforced systems, the subject matter of which is incorporated herein by reference the same as if set forth at length. Since reinforced resin systems made in accordance with the present invention may be heated to well in excess of one thousand degrees Fahrenheit, porcelain replacement teeth, which are required to be fired in ovens, may be formed utilizing the ceramic fiber reinforced resin systems of the present invention.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A method of forming a reinforced resin system, comprising the steps of:
   etching a ceramic fiber material;
   silanating the etched ceramic fiber material; and
   applying a resin to the etched, silanated ceramic fiber material.

2. A method in accordance with claim 1 wherein the etching step is performed using hydrofluoric acid.

3. A method in accordance with claim 1 wherein the etching step is performed using acidulated phosphate fluoride.

4. A method in accordance with claim 1 wherein said silanating step is performed by using an organo-functional silane selected from the group consisting of vinyltrichlorosilane, vinyltriethoxysilane, vinyl-tris(beta-methoxyethoxy)silane, gamma-Methacryloxypropyltrimethoxysilane, beta-(3,4-Epoxycyclohexyl)-ethyltrimethoxysilane, gamma-Glycidoxypropyltrimethoxysilane, gamma-Aminopropyltriethoxysilane, and N-beta-(aminoethyl)-gamma-aminopropyltrimethoxysilane.

5. A method in accordance with claim 1 wherein said ceramic fiber material is selected to be in the form of ceramic fiber cloth.

6. A method in accordance with claim 1 wherein said ceramic fiber material is selected to be in the form of a mesh.

7. A method in accordance with claim 1 wherein said ceramic fiber material is selected to be in the form of a rope or thread.

8. A method in accordance with claim 1 wherein said resin is selected to be a thermoplastic resin.

9. A method in accordance with claim 1 wherein said resin is selected to be a thermosetting resin.

10. A method in accordance with claim 1 wherein said ceramic fiber material is comprised of a fiber having a ceramic surface and a core of another material.

11. A product for producing an improved reinforced or filled resin system, comprising:
    an etched ceramic fiber material, said ceramic fiber material being etched with a compound selected from the group consisting of hydrofluoric acid and acidulated phosphate fluoride to increase the strength of the bonding between the ceramic fibers and the resinous material applied to the ceramic fibers.

12. A product in accordance with claim 11 wherein said etched ceramic fiber material is silanated with an organo-functional silane.

13. A product in accordance with claim 12 wherein said organo-functional silane is selected from the group consisting of vinyltrichlorosilane, vinyltriethoxysilane, vinyl-tris(beta-methoxyethoxy)silane, gamma-Methacryloxypropyltrimethoxysilane, beta-(3,4-Epoxycyclohexyl)-ethyltrimethoxysilane, gamma-Glycidoxypropyltrimethoxysilane, gamma-Aminopropyltriethoxysilane, and N-beta-(aminoethyl)-gamma-aminopropyltrimethoxysilane.

14. A product in accordance with claim 11 wherein said ceramic fiber material is selected to be in the form of ceramic fiber cloth.

15. A product in accordance with claim 11 wherein said ceramic fiber material is selected to be in the form of a mesh.

16. A product in accordance with claim 11 wherein said ceramic fiber material is selected to be in the form of a rope or thread.

17. A product in accordance with claim 11 wherein a ceramic fiber reinforced or filled resin system is constructed utilizing a thermoplastic resin.

18. A product in accordance with claim 11 wherein a ceramic fiber reinforced or filled resin system is constructed utilizing a thermosetting resin.

19. A product in accordance with claim 11 wherein said etched ceramic fiber material is comprised of an etched surface of ceramic material and a core of another material.

20. An article of manufacture, comprising:
    a material for use in dental processes involving the reconstruction or stabilization of one or more teeth, comprising an etched ceramic fiber material treated with an organo-functional silane.

21. A material in accordance with claim 20 wherein said ceramic fiber material is in the form of a mesh.

22. A material in accordance with claim 20 wherein said ceramic fiber material is in the form of thread or rope.

23. An article of manufacture, comprising:

a material for use in dental processes involving the reconstructional or stabilization of one or more teeth, comprising a textile material in the form of a mesh, cloth, rope or thread constructed or ceramic fibers, such textile material being etched and adapted for embedding in a moldable dental material in the form of a dental resin or ceramic material.

24. An article or manufacture in accordance with claim 23 wherein said etched textile material is silanated.

25. A method, comprising the steps of:

selecting a textile material constructed of ceramic fibers in the form of a mesh, cloth rope or thread for use in reconstructing or stabilizing one or more teeth;

etching the textile material; and utilizing said etched textile material of ceramic fiber embedded as a reinforcement in a moldable resin or ceramic material for the reconstruction or stabilization of one or more teeth.

26. A method of accordance with claim 25 including the step of silanating the etched textile material prior to embedding the textile material as a reinforcement.

* * * * *

UNITED STATES PATENT AND TRADEMARK OFFICE
CERTIFICATE OF CORRECTION

PATENT NO. : 5,425,640
DATED : June 20, 1995
INVENTOR(S) : Jonathan Scharf It is certified that error appears in the above-identified patent and that said Letters Patent is hereby corrected as shown below:

Column 6, line 10, delete "of", insert --in--.

Signed and Sealed this

Twelfth Day of September, 1995

Attest:

BRUCE LEHMAN

*Attesting Officer*  *Commissioner of Patents and Trademarks*